(12) United States Patent
Lau

(10) Patent No.: US 7,174,896 B1
(45) Date of Patent: Feb. 13, 2007

(54) METHOD AND APPARATUS FOR SUPPORTING A HEART

(75) Inventor: Lilip Lau, Sunnyvale, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 681 days.

(21) Appl. No.: 10/338,934

(22) Filed: Jan. 7, 2003

Related U.S. Application Data

(60) Provisional application No. 60/346,788, filed on Jan. 7, 2002.

(51) Int. Cl.
*A61F 2/00* (2006.01)
*A61B 19/00* (2006.01)

(52) U.S. Cl. .......................................... 128/898; 600/37

(58) Field of Classification Search .................. 600/37, 600/16–18; 128/898, 897
See application file for complete search history.

(56) References Cited

U.S. PATENT DOCUMENTS

| | | | |
|---|---|---|---|
| 2,278,926 A | 4/1942 | Hartwell |
| 2,826,193 A | 3/1958 | Vineberg |
| 3,464,322 A | 9/1969 | Pequignot |
| 3,513,836 A | 5/1970 | Sausse |
| 3,587,567 A | 6/1971 | Schiff |
| 3,613,672 A | 10/1971 | Schiff |
| 3,966,401 A | 6/1976 | Hancock et al. |
| 3,983,863 A | 10/1976 | Janke et al. |
| 3,988,782 A | 11/1976 | Dardik et al. |
| 4,011,947 A | 3/1977 | Sawyer |
| 4,048,990 A | 9/1977 | Goetz |
| 4,065,816 A | 1/1978 | Sawyer |
| 4,108,161 A | 8/1978 | Samuels et al. |
| 4,192,293 A | 3/1980 | Asrican |
| 4,211,325 A | 7/1980 | Wright |
| 4,261,342 A | 4/1981 | Aranguren Duo |
| 4,306,318 A | 12/1981 | Mano et al. |
| 4,372,293 A | 2/1983 | Vijil-Rosales |
| 4,403,604 A | 9/1983 | Wilkinson et al. |
| 4,428,375 A | 1/1984 | Ellman |
| 4,512,471 A | 4/1985 | Kaster et al. |
| 4,536,893 A | 8/1985 | Parravicini |
| 4,545,783 A | 10/1985 | Vaughn |
| 4,628,937 A | 12/1986 | Hess et al. |
| 4,630,597 A | 12/1986 | Kantrowitz et al. |

(Continued)

FOREIGN PATENT DOCUMENTS

DE 3831 540 A1 4/1989

(Continued)

OTHER PUBLICATIONS

Bencini, Adriano, M.D., *The "Pneumomassage" of the Heart*, Surgery, vol. 39, No. 3, Mar. 1956.

(Continued)

*Primary Examiner*—Samuel G. Gilbert
(74) *Attorney, Agent, or Firm*—Fulwider Patton LLP

(57) ABSTRACT

A method and apparatus for treating heart failure includes applying a bioabsorbable material around at least a portion of a patient's heart. The bioabsorbable material can be applied in conjunction with a nonbioabsorbable structure such as a cardiac harness or in lieu of such a harness. The harness and/or bioabsorbable material is configured to apply a mild compressive force on the heart.

4 Claims, 7 Drawing Sheets

U.S. PATENT DOCUMENTS

| | | |
|---|---|---|
| 4,665,906 A | 5/1987 | Jervis |
| 4,690,134 A | 9/1987 | Snyders |
| 4,697,703 A | 10/1987 | Will |
| 4,750,619 A | 6/1988 | Cohen et al. |
| 4,821,723 A | 4/1989 | Baker, Jr. et al. |
| 4,827,932 A | 5/1989 | Ideker et al. |
| 4,834,707 A | 5/1989 | Evans |
| 4,838,288 A | 6/1989 | Wright et al. |
| 4,840,626 A | 6/1989 | Linsky et al. |
| 4,863,016 A | 9/1989 | Fong et al. |
| 4,878,890 A | 11/1989 | Bilweis |
| 4,936,857 A | 6/1990 | Kulik |
| 4,957,477 A | 9/1990 | Lundbäck |
| 4,960,424 A | 10/1990 | Grooters |
| 4,973,300 A | 11/1990 | Wright |
| 4,976,730 A | 12/1990 | Kwan-Gett |
| 5,031,762 A | 7/1991 | Heacox |
| 5,057,117 A | 10/1991 | Atweh |
| 5,067,957 A | 11/1991 | Jervis |
| 5,087,243 A | 2/1992 | Avitall |
| 5,456,711 A | 10/1995 | Hudson |
| 5,713,954 A | 2/1998 | Rosenberg et al. |
| 5,727,569 A | 3/1998 | Benetti et al. |
| 5,749,839 A | 5/1998 | Kovacs |
| 5,782,746 A | 7/1998 | Wright |
| 5,800,334 A | 9/1998 | Wilk |
| 5,800,528 A | 9/1998 | Lederman et al. |
| 5,814,097 A | 9/1998 | Sterman et al. |
| 5,824,028 A | 10/1998 | Knisley |
| 5,836,311 A | 11/1998 | Borst et al. |
| 5,848,962 A | 12/1998 | Feindt et al. |
| 5,849,005 A | 12/1998 | Garrison et al. |
| 5,853,422 A | 12/1998 | Huebsch et al. |
| 5,865,791 A | 2/1999 | Whayne et al. |
| 5,876,432 A | 3/1999 | Lau et al. |
| 5,904,690 A | 5/1999 | Middleman et al. |
| 5,910,124 A | 6/1999 | Rubin |
| 5,927,284 A | 7/1999 | Borst et al. |
| 5,948,019 A | 9/1999 | Shu et al. |
| 5,957,977 A | 9/1999 | Melvin |
| 5,961,440 A | 10/1999 | Schweich, Jr. et al. |
| 5,976,069 A | 11/1999 | Navia et al. |
| 5,979,456 A | 11/1999 | Magovern |
| 5,984,857 A | 11/1999 | Buck et al. |
| 5,990,378 A | 11/1999 | Ellis |
| 6,007,486 A | 12/1999 | Hunt et al. |
| 6,015,378 A | 1/2000 | Borst et al. |
| 6,024,096 A | 2/2000 | Buckberg |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,076,013 A | 6/2000 | Brennan et al. |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,095,968 A | 8/2000 | Snyders |
| 6,110,100 A | 8/2000 | Talpade |
| 6,117,159 A | 9/2000 | Huebsch et al. |
| 6,117,979 A | 9/2000 | Hendriks et al. |
| 6,123,662 A | 9/2000 | Alferness et al. |
| 6,125,852 A | 10/2000 | Stevens et al. |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,166,184 A | 12/2000 | Hendriks et al. |
| 6,169,922 B1 | 1/2001 | Alferness et al. |
| 6,174,279 B1 | 1/2001 | Girard |
| 6,179,791 B1 | 1/2001 | Krueger |
| 6,183,411 B1 | 2/2001 | Mortier et al. |
| 6,190,408 B1 | 2/2001 | Melvin |
| 6,193,648 B1 | 2/2001 | Krueger |
| 6,206,820 B1 | 3/2001 | Kazi et al. |
| 6,214,047 B1 | 4/2001 | Melvin |
| 6,217,894 B1 | 4/2001 | Sawhney et al. |
| 6,221,103 B1 | 4/2001 | Melvin |
| 6,224,540 B1 | 5/2001 | Lederman et al. |
| 6,230,714 B1 | 5/2001 | Alferness et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,282,445 B1 | 8/2001 | Reinhardt et al. |
| 6,287,250 B1 | 9/2001 | Peng et al. |
| 6,293,906 B1 | 9/2001 | Vanden Hoek et al. |
| 6,306,141 B1 | 10/2001 | Jervis |
| 6,312,725 B1 | 11/2001 | Wallace et al. |
| 6,352,710 B2 | 3/2002 | Sawhney et al. |
| 6,360,749 B1 | 3/2002 | Jayaraman |
| 6,375,608 B1 | 4/2002 | Alferness |
| 6,390,976 B1 | 5/2002 | Spence et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1 | 8/2002 | Wardle |
| 6,451,025 B1 | 9/2002 | Jervis |
| 6,482,146 B1 | 11/2002 | Alferness et al. |
| 6,517,570 B1 | 2/2003 | Lau et al. |
| 6,537,203 B1 | 3/2003 | Alferness et al. |
| 6,544,168 B2 | 4/2003 | Alferness |
| 6,547,821 B1 * | 4/2003 | Taylor et al. ................. 623/3.1 |
| 6,564,094 B2 | 5/2003 | Alferness et al. |
| 6,567,699 B2 | 5/2003 | Alferness et al. |
| 6,569,082 B1 | 5/2003 | Chin |
| 6,659,082 B1 | 5/2003 | Chin |
| 6,572,533 B1 | 6/2003 | Shapland et al. |
| 6,575,921 B2 | 6/2003 | Vanden Hoek et al. |
| 6,582,355 B2 | 6/2003 | Alferness et al. |
| 6,585,733 B2 * | 7/2003 | Wellman ..................... 606/41 |
| 6,587,734 B2 | 7/2003 | Okuzumi |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,633,780 B1 | 10/2003 | Berger |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,689,048 B2 | 2/2004 | Vanden Hoek et al. |
| 6,695,769 B2 | 2/2004 | French et al. |
| 6,699,259 B2 | 3/2004 | Fogarty et al. |
| 6,701,929 B2 | 3/2004 | Hussein |
| 6,702,732 B1 | 3/2004 | Lau et al. |
| 6,723,041 B2 | 4/2004 | Lau et al. |
| 6,730,016 B1 | 5/2004 | Cox et al. |
| 6,759,431 B2 | 7/2004 | Hunter et al. |
| 6,818,018 B1 | 11/2004 | Sawhney |
| 6,833,408 B2 | 12/2004 | Sehl et al. |
| 6,876,887 B2 | 4/2005 | Okuzumi |
| 6,881,185 B2 | 4/2005 | Vanden Hock et al. |
| 6,887,192 B1 | 5/2005 | Whayne et al. |

| | | |
|---|---|---|
| 6,893,392 B2 | 5/2005 | Alferness |
| 6,896,652 B2 | 5/2005 | Alferness et al. |
| 6,902,522 B1 | 6/2005 | Walsh et al. |
| 6,902,524 B2 | 6/2005 | Alferness et al. |
| 6,908,426 B2 | 6/2005 | Shapland et al. |
| 2001/0029314 A1 | 10/2001 | Alferness et al. |
| 2001/0047122 A1 | 11/2001 | Vanden Hoek et al. |
| 2002/0007216 A1 | 1/2002 | Melvin |
| 2002/0022880 A1 | 2/2002 | Melvin |
| 2002/0068849 A1 | 6/2002 | Schweich, Jr. et al. |
| 2002/0077524 A1 | 6/2002 | Schweich, Jr. et al. |
| 2002/0082647 A1 | 6/2002 | Alferness et al. |
| 2002/0091296 A1 | 7/2002 | Alferness |
| 2002/0103511 A1 | 8/2002 | Alferness et al. |
| 2002/0151950 A1 | 10/2002 | Okuzumi |
| 2003/0060674 A1 | 3/2003 | Gifford, III et al. |
| 2003/0060677 A1 | 3/2003 | French et al. |
| 2003/0060895 A1 | 3/2003 | French et al. |
| 2003/0163111 A1* | 8/2003 | Daellenbach ............ 604/500 |
| 2003/0199733 A1 | 10/2003 | Shapland et al. |
| 2003/0199955 A1 | 10/2003 | Struble et al. |
| 2003/0229265 A1 | 12/2003 | Girard et al. |
| 2004/0015041 A1* | 1/2004 | Melvin .................... 600/16 |
| 2004/0133069 A1 | 7/2004 | Shapland et al. |
| 2004/0138521 A1* | 7/2004 | Grabek et al. ............ 600/37 |
| 2004/0171907 A1 | 9/2004 | Alferness et al. |
| 2004/0171908 A1 | 9/2004 | Alferness et al. |
| 2005/0059854 A1 | 3/2005 | Hoek et al. |
| 2005/0085688 A1 | 4/2005 | Girard et al. |

FOREIGN PATENT DOCUMENTS

| | | |
|---|---|---|
| DE | 38 31 540 C2 | 6/1993 |
| DE | 295 17 393 U1 | 3/1996 |
| EP | 0 370 931 A1 | 5/1990 |
| EP | 0 280 564 B1 | 6/1993 |
| EP | 0 583 012 B1 | 7/1996 |
| FR | 2 527 435 | 12/1983 |
| FR | 2 645 739 | 10/1990 |
| GB | 2 115 287 A | 9/1983 |
| GB | 2 209 678 A | 5/1989 |
| JP | 60-203250 | 10/1985 |
| JP | 1-145066 | 6/1989 |
| JP | 1-271829 | 10/1989 |
| SU | 1009457 A | 4/1983 |
| SU | 1734767 A1 | 5/1992 |
| WO | WO 91/19465 | 12/1991 |
| WO | WO 95/06447 | 3/1995 |
| WO | WO 96/04852 | 2/1996 |
| WO | WO 98/58598 | 12/1998 |
| WO | WO 00/06027 | 2/2000 |
| WO | WO 00/06028 | 2/2000 |
| WO | WO 00/13722 | 3/2000 |
| WO | WO 00/16700 | 3/2000 |
| WO | WO 00/18320 | 4/2000 |
| WO | WO 00/28912 | 5/2000 |
| WO | WO 00/28918 | 5/2000 |
| WO | WO 00/0036995 | 6/2000 |
| WO | WO 00/42919 | 7/2000 |
| WO | WO 00/45735 | 8/2000 |
| WO | WO 00/48795 | 8/2000 |
| WO | WO 00/62727 | 10/2000 |
| WO | WO 00/74769 | 12/2000 |
| WO | WO 01/17437 | 3/2001 |
| WO | WO 01/21098 | 3/2001 |
| WO | WO 01/50981 | 7/2001 |
| WO | WO 01/67985 | 9/2001 |
| WO | WO 01/85061 | 11/2001 |
| WO | WO 01/91667 | 12/2001 |
| WO | WO 01/95830 | 12/2001 |
| WO | WO 01/95831 | 12/2001 |
| WO | WO 01/95832 | 12/2001 |
| WO | WO 02/13726 | 2/2002 |
| WO | WO 02/19917 | 3/2002 |
| WO | WO 02/059007 | 8/2002 |
| WO | WO 03/026483 | 4/2003 |
| WO | WO 03/026484 | 4/2003 |
| WO | WO 03/026485 | 4/2003 |

OTHER PUBLICATIONS

Anstadt, George L., et al., *A New Instrument for Prolonged Mechanical Cardiac Massage*, Abstracts of the 38th Scientific Sessions, Supplement II to *Circulation*, vols. 31 and 32, pp. 375-384, Oct. 1965.

Paling, D.F., *Warp Knitting Technology*, 1970.

Edie, Richard N., M.D., et al., *Surgical Repair of Single Ventricle*, The Journal of Thoracic and Cardiovascular Surgery, vol. 66, No. 3, pp. 350-360, Sep. 1972.

McGoon, Dwight C., M.D., et al., *Correction of the Univentricular Heart Having Two Atriovantricular Valves*, The Journal of Thoracic and Cardiovascular Surgery, vol. 74, No. 2, pp. 218-226, Aug. 1977.

Doty, Donald B., et al., *Septation of the Univentricular Heart: Transatrial Approach*, The Journal of Thoracic and Cardiovascular Surgery, vol. 78, No. 3, pp. 424-430, Sep. 1979.

Schetky, L. McDonald, *Shap- Memory Alloys*, Scientific American, vol. 241, No. 5, pp. 74-82, Nov. 1979.

Melton, K.N., et al., *Alloys With Two-Shape Memory Effect*, Mechanical Engineering, pp. 42-43, Mar. 1980.

Feldt, Robert H., M.D., et al., *Current Status of the Septation Procedure for Univentricular Heart*, The Journal of Thoracic and Cardiovascular Surgery, vol. 82, No. 1, pp. 93-97, Jul. 1981.

Carpenter, A., et al., *Myocardial Substitution With Stimulated Skeletal Muscle: First Successful Clinical Case*, The Lancet, Jun. 1, 1985.

Anstadt, Mark P. et al., *Direct Mechanical Ventricular Actuation: A Review*, Resuscitation, pp. 7-23, 1991.

Anstadt, Mark P., M.D., et al., *Pulsatile Reperfusion After Cardiac Arrest Improves Neurologic Outcome*, American Surgery, vol. 214, No. 4, pp. 478-490, Oct. 1991.

Schumacker, Harris B., Jr., *Chapter 21: Cardiac Aneurysms*, The Evolution of Cardiac Surgery, pp. 159-165, 1992.

Savage, Edward B., M.D., et al., *Repair of Left Ventricular Aneurysm*, The Journal of Thoracic and Cardiovascular Surgery, vol. 104, No. 3, pp. 752-762, Sep. 1992.

Carpentier, Alain, M.D., Ph.D., et al., *Dynamic Cardiomyoplasty at Seven Years*, The Journal of Thoracic and Cardiovascular Surgery, vol. 106, No. 1, pp. 42-54, Jul. 1993.

Capouya, Eli R., M.D., et al., *Girdling Effect of Nonstimulated Cardiomyoplasty on Left Ventricular Function*, Annals of Thoracic Surgeons, vol. 56, pp. 867-871, 1993.

Chekanov, Valeri, M.D., Ph.D., *Nonstimulated Cardiomyoplasty Wrap Attenuated the Degree of Left Ventricular Enlargement*, Annals of Thoracic Surgeons, vol. 57, pp. 1684-1690, 1997.

Chiu, Ray C.-J. *Using Skeletal Muscle for Cardiac Assistance*, Scientific American, pp. 68-77, Nov./Dec. 1994.

Kass, David A., M.D., et al., *Reverse Remodeling From Cardiomyoplasty in Human Heart Failure: External Constraint Versus Active Assist*, Circulation, vol. 91, No. 9, pp. 2314-2318, May 1, 1995.

Vaynblat, Mikhail, M.D., et al., *Cardiac Binding in Experimental Heart Failure*, Annals of Thoracic Surgery (Abstract), Supplement to *Circulation*, vol. 92, Suppl. 1, 1995.

Levin, Howard R., M.D., et al., *Reversal of Chronic Ventricular Dilation in Patients With End-Stage Cardiomyopathy by Prolonged Mechanical Unloading*, Circulation, vol. 91, No. 11, pp. 2717-2720, 1995.

Chaudhry, Pervaiz A., M.D., et al., *Acute Ventricular Reduction with Acorn's Cardiac Support Device Prevents Progressive Left Ventricular Dysfunction and Remodeling in Dogs With Advanced Heart Failure*, Cardiothoracic Surgery, pp. 146-148, 1996.

Oh, Joong Hwan, M.D., et al., *Mechanisms of Dynamic Cardiomyoplasty: Current Concepts*, Journal of Cardiac Surgery, vol. 11, pp. 194-199, 1996.

Wood, Alastair J.J., M.D., Editor, Review of Cohn, Jay N., M.D., *The Management of Chronic Heart Failure*, The New England Journal of Medicine: Review Article, vol. 335, No. 7, pp. 490-498, Aug. 15, 1996.

Badhwar, Vinay, *Power Generation From Four Skeletal Muscle Configurations Design Implications for a Muscle Powered Cardiac Assist Device*, ASAIO Journal, vol. 43, pp. M651-M657, 1997.

Vaynblat, Mikhail, M.D., et al., *Cardiac Binding in Experimental Heart Failure*, Annals of Thoracic Surgery, vol. 64, pp. 81-85, 1997.

Westaby, Stephen, et al., *Landmarks in Cardiac Surgery*, pp. 198-199, 1997.

Cox, James L., *Left Ventricular Aneurysms: Pathophysiologic Observations and Standard Resection*, Seminars in Thoracic Cardiovascular Surgery, vol. 9, No. 2, pp. 113-122, Apr. 1997.

Coletta, C., et al., *Prognostic Value of Left Ventricular Volume Response During Dobutamine Stress Echocardiography*, European Heart Journal, vol. 18, pp. 1599-1603, Oct. 1997.

Capomolla, Soccorso, M.D., et al., *Dobutamine and Nitroprusside Infusion in Patients With Severe Congestive Heart Failure: Hemodynamic Improvement by Discordant Effects on Mitral Regurgitation, Left Atrial Function, and Ventricular Function*, American Heart Journal, 1089-1098, Dec. 1997.

Oh, Joong Hwan, *The Effects of Prosthetic Cardiac Binding and Adynamic Cardiomyoplasty in a Model of Dilated Cardiomyopathy*, The Journal of Thoracic and Cardiovascular Surgery, vol. 116, No. 1, pp. 148-153, 1998.

Cohn, Jay N., M.D., *Preventing Congestive Heart Failure*, American Family Physician, 6 pages, Apr. 15, 1998.

Cohn, Jay N., M.D., *Structural Basis for Heart Failure: Ventricular Remodeling and Its Pharmacological Inhibition*, Circulation, vol. 91, No. 10, pp. 2504-2507, May 15, 1995.

Gaudron, Peter, M.D., et al., *Progressive Left Ventricular Dysfunction and Remodeling After Myocardial Infarction*. Circulation, vol. 87, pp. 755-763, Mar. 1993.

Pfeiffer, Marc A., M.D., et al., *Ventricular Remodeling After Myocardial Infarction: Experimental Observations and Clinical Implications*, Circulation, vol. 81, No. 4, pp. 1161-1172, Apr. 1990.

Guasp, Francisco Torrent, *Una protesis contentiva para el tratamiento de la microcardiopatia dilatads*, Revista Española de Cardiologia, vol. 51, No. 7, Jul. 1998.

Power, J.M., et al., *Passive Ventricular Constraint Amends the Course of Heart Failure: A Study in an Ovine Model of Dilated Cardiomyopathy*, Cardiovascular Research, vol. 44, pp. 549-555, 1999.

Frazier, O.H., M.D., et al., *Left Ventricular Assist System as a Bridge to Myocardial Recovery*, Annals of Thoracic Surgery, vol. 68, pp. 734-741, 1999.

Melvin, David B., *Ventricular Radium Reduction Without Resection: A Computational Analysis*, ASAIO Journal, 160-165, 1999.

*ABSTRACTS—Heart Failure*, JACC Feb. 1999.

Raman, Jai S., Fracs, et al., *Ventricular Containment as an Adjunctive Procedure in Ischemic Cardiomyopathy: Early Results*, Annals of Thoracic Surgery, vol. 70, pp. 1124-1126, Jan. 2000.

McCarthy, Patrick M., et al., *Device Based Left Ventricular Shape Change Immediately Reduces Left Ventricular Volume and Increases Ejection Fraction in a Pacing Induced Cardiomyopathy Model in Dogs*, JACC, Feb. 2000.

Chaudhry, Pervaiz A., M.D., et al., *Passive Epicardial Containment Prevents Ventricular Remodeling in Heart Failure*, Annals of Thoracic Surgeons, vol. 70, pp. 1275-1280, 2000.

Acorn Cardiovascular, Inc., *CSD Specifications Acorn Cardiac Support Device*, 2000.

*Heart "jacket" could help stop heart failure progression*, Clinicia, No. 916, Jul. 2000.

Acorn Cardiovascular, Inc., *CorCap™ Cardiac Support Device Pamphlet*, Jun. 2001.

*Medtronic's InSync Cardiac Resynchronization Therapy Device Approved by FDA*, (Press Release) Aug. 28, 2001.

Acorn Cardiovascular, Inc., *Acorn Highlights: ESC, Schedule*, Sep. 2001.

Oz, Mehmet C., M.D., *Passive Ventricular Constraint for the Treatment of Congestive Heart Failure*, Annals of Thoracic Surgery, vol. 71, pp. 5185-5187, 2001.

*Abstract Supplement*, European Heart Journal, vol. 22, Sep. 2001.

Gorman, J., *Self-Sutures: New Material Knots Up On Its Own*, Science News, vol. 161, p. 262, Apr. 27, 2002.

Mann, Douglas L., M.D., *Basic Mechanisms of Remodeling and Reverse Remodeling*, presented at 6th Annual Scientific Meeting of the Heart Failure Society of America, Sep. 24, 2002.

Bocchi, Edimar a., M.D., *Arrhythmias and Sudden Death After Dynamic Cardiomyoplasty*, Circulation, vol. 90, No. 5, Part 2, pp. II-107 thru II-111, Nov. 1994.

Cachques, Juan C., M.D., *Study of Muscular and Ventricular Function in Dynamic Cardiomyoplasty: A Ten-Year Follow-Up*, The Journal of Heart and Lung Transplantation, vol. 16, No. 8, pp. 854-868, Aug. 1997.

Dullum, Mercedes K.C., M.D., et al., *Less Invasive Surgical Management of Heart Failure by Cardiac Support Device Implantation on the Beating Heart*, The Heart Surgery Forum, #2001-1818, pp. 361-363, Jan. 4-7, 2001.

Macris, Michael P. M.D., et al., *Minimally Invasive Access of the Normal Preicardium: Initial Clinical Experience with a Novel Device*, Clinical Cardiology, vol. 22 (Suppl. 1), pp. I-36, thru I-39, 1999.

Thakur, Ranjan K., M.D., et al., *Latissimus Dorsi Dynamic Cardiomyoplasty: Role of Combined ICD Implantation*, Journal of Cardiac Surgery, vol. 10, pp. 295-297, 1995.

Application for U.S. Appl. No. 09/634,043, filed Aug. 8, 2000.
Application for U.S. Appl. No. 09/952,145, filed Sep. 10, 2001.
Application for U.S. Appl. No. 10/242,016, filed Sep. 10, 2002.
Application for U.S. Appl. No. 10/287,723, filed Oct. 31, 2002.
Application for U.S. Appl. No. 10/314,696, filed Dec. 9, 2002.
Application for U.S. Appl. No. 10/338,934, filed Jan. 7, 2003.
U.S. Appl. No. 60/458,991, filed Mar. 28, 2003.
U.S. Appl. No. 60/486,062, filed Jul. 10, 2003.
Application for U.S. Appl. No. 10/693,577, filed Oct. 23, 2003.
Application for U.S. Appl. No. 10/694,646, filed Oct. 27, 2003.
Application for U.S. Appl. No. 10/698,237, filed Oct. 31, 2003.
Application for U.S. Appl. No. 10/704,376, filed Nov. 7, 2003.
Application for U.S. Appl. No. 10/705,989, filed Nov. 12, 2003.
Application for U.S. Appl. No. 10/714,189, filed Nov. 13, 2003.
Application for U.S. Appl. No. 10/715,150, filed Nov. 17. 2003.
Application for U.S. Appl. No. 10/754,174, filed Jan. 9, 2004.
Application for U.S. Appl. No. 10/754,264, filed Jan. 9, 2004.
Application for U.S. Appl. No. 10/754,852, filed Jan. 9, 2004.
U.S. Appl. No. 60/535,888, filed Jan. 12, 2004.
Application for U.S. Appl. No. 10/777,451, filed Feb. 12, 2004.
Application for U.S. Appl. No. 10/788,791, filed Feb. 27, 2004.
Application for U.S. Appl. No. 10/704,376, filed Mar. 3, 2004.
Application for U.S. Appl. No. 10/705,574, filed Mar. 5, 2004.

Zhou, Xiaohong, et al., *Epicardial Mapping of Ventricular Defibrillation With Monophasic and Biphasic Shocks in Dogs*, Circulation Research, vol. 72, No. 1, pp. 145-160, Jan. 1993.

Shorofsky, Stephen R., et al., *Comparison of Step-Down and Binary Search Algorithms for Determination of Defibrillation Threshold in Humans*, PACE, vol. 27, pp. 218-220, Feb. 2004.

Gold, Michael R., M.D., et al., *Comparison of Single- and Dual-Coil Active Pectoral Defibrillation Lead Systems*, Journal of the American College of Cardiology, vol. 31, No. 6, pp. 1391-1394, May 1998.

Rinaldi, C. Aldo, *A Randomized Prospective Study of Single Coil Versus Dual Coil Defibrillation in Patients With Ventricular Arrhythmias Undergoing Implantable Cardioverter Defibrillator Therapy*, PACE, vol. 26, pp. 1684 1690, Aug. 2003.

Schwartzman, David, M.D., et al., *Serial Defibrillation Lead Impedance in Patients with Epicardial and Nonthoracotomy Lead Systems*, Journal of Cardiovascular Electrophysiology, vol. 7, No. 8, pp. 697-703, Aug. 1996.

Sandstedt, Bengt, et al., *Bidirectioinal Defibrillation Using Implantable Defibrillators: A Prospective Randomized Comparison Between Pectoral and Abdominal Active Generators*, PACE, vol .24, Part 1, pp. 1343-1353, Sep. 2001.

Schulte, B., et al., *Dual-Coil vs. Single-Coil Active Pectoral Implantable Defibrillator Lead Systems: Defibrillation Lead Requirements and Probability of Defibrillation Success at Multiples of the Defibrillation Energy Requirements*, Europace, vol. 3, pp. 177-180, Jul. 2001.

Cohn, Jay N., M.D., *Drug Therapy*, The New England Journal of Medicine, pp. 490-498, Aug. 15, 1996.

Wharton, J. Marcus et al., *Electrophysiological Effects of Monophasic and Biphasic Stimuli in Normal and Infarcted Dogs*, PACE, vol. 13, pp. 1158-1172, Sep. 1990.

Shabetai, Ralph, *The Role of the Pericardium in the Pathophysiology of Heart Failure, Congestive Heart Failure*, Second Edition, Chapter 9, pp. 157-187, 2000.

\* cited by examiner

METHOD AND APPARATUS FOR SUPPORTING A HEART

RELATED APPLICATION

This application is based on and claims priority to U.S. Provisional Application No. 60/346,788, filed Jan. 7, 2002, the entirety of which is hereby incorporated by reference.

FIELD OF THE INVENTION

This application relates to a method and apparatus for treating congestive heart failure, and more specifically relates to methods and apparatus using bioabsorbable material to treat congestive heart failure.

BACKGROUND OF THE INVENTION

Congestive heart failure ("CHF") is characterized by the failure of the heart to pump blood at sufficient flow rates to meet the metabolic demand of tissues, especially the demand for oxygen. One characteristic of CHF is remodeling of at least portions of a patient's heart. Remodeling involves physical changes to the size, shape and thickness of the heart wall. For example, a damaged left ventricle may have some localized thinning and stretching of a portion of the myocardium. The thinned portion of the myocardium often is functionally impaired, and other portions of the myocardium attempt to compensate. As a result, the other portions of the myocardium may expand so that the stroke volume of the ventricle is maintained notwithstanding the impaired zone of the myocardium. Such expansion may cause the left ventricle to assume a somewhat spherical shape.

Cardiac remodeling often subjects the heart wall to increased wall tension or stress, which further impairs the heart's functional performance. Often, the heart wall will dilate further in order to compensate for the impairment caused by such increased stress. Thus, a vicious cycle can result, in which dilation leads to further dilation and greater functional impairment.

Historically, congestive heart failure has been managed with a variety of drugs. Devices have also been used to improve cardiac output. For example, left ventricular assist pumps help the heart to pump blood. Multi-chamber pacing has also been employed to optimally synchronize the beating of the heart chambers to improve cardiac output. Skeletal muscle, such as the latissimus dorsi, has been used to assist ventricular pumping. Researchers and cardiac surgeons have also experimented with prosthetic "girdles" disposed around the heart. One such design is a prosthetic "sock" or "jacket" that is wrapped around the heart. Presently, a device is being marketed as the CorCap™, available from Acorn, Inc. The CorCap™ apparatus comprises a woven and/or knitted sock-like device that restricts cardiac expansion beyond a predetermined size.

Although some of the above-discussed devices hold promise, there remains a need in the art for an improved method and apparatus for treating CHF to prevent a remodeled heart from further remodeling and/or to help reverse remodeling of a diseased heart.

SUMMARY OF THE INVENTION

In accordance with one aspect of the present invention, a method for treating heart failure comprises introducing a substance adjacent the patient's heart so as to stimulate growth of scar tissue about the heart so that the scar tissue at least partially encapsulates the heart and resists expansion of the heart beyond a predetermined size.

In accordance with another aspect of the present invention, a method of treating cardiac failure comprises providing a cardiac wall tension reduction device configured to fit at least partially around the heart and to exert a generally inwardly directed force on the heart during at least a portion of the cardiac cycle. The wall tension reduction device is formed of a bioabsorbable material and is combined with medicaments for restricting growth of scar tissue by the patient's body. The cardiac wall tension reduction device is positioned about the heart so that the tension reduction device reduces the load on the heart until the device dissolves.

In accordance with another aspect, the present invention provides a cardiac wall tension reduction device for treating heart failure of a patient. A first member is configured to fit generally around a portion of the patient's heart and is configured to apply a pressure to the heart. A second member is configured to fit generally around a portion of the patient's heart and is configured to apply a second pressure to the heart. The second pressure is greater than the first pressure. The second member is constructed of a bioabsorbable material and is adapted to dissolve over time within the patient's body, while the first member is constructed of a substantially durable material that will remain in place after the second member dissolves.

In accordance with still another aspect, the present invention provides a cardiac harness configured to fit generally around a patient's heart and to resist expansion of the patient's heart beyond a desired size by applying a mild compressive force on the heart. The harness is adapted to expand and contract with the heart. A change in size of the harness of about 20% within an operating range of the harness corresponds to a change in pressure applied by the harness of less than about 4 mmHg.

DESCRIPTION OF PREFERRED EMBODIMENTS

This application presents a method and apparatus for supporting a patient's diseased heart in order to resist and possibly reverse remodeling of the heart. As discussed in the co-pending application entitled "Expandable Cardiac Harness For Treating Congestive Heart Failure", Ser. No. 09/634,043, which was filed on Aug. 8, 2000, the entirety of which is hereby expressly incorporated by reference, it is anticipated that remodeling of a diseased heart can be resisted or even reversed by alleviating the wall stresses in such a heart. The present application discusses certain embodiments and methods for supporting the cardiac wall. Additional embodiments and aspects are also discussed in Applicants' co-pending applications entitled "Device for Treating Heart Failure," Ser. No. 10/242,016, filed Sep. 10, 2002, "Heart Failure Treatment Device and Method", Ser. No. 70/287,723, filed Oct. 31, 2002, and "Method and Apparatus for Treating Heart Failure," Ser. No. 60/409,113, filed Sep. 5, 2002. The entirety of each of these applications are hereby expressly incorporated by reference.

Figure 1:
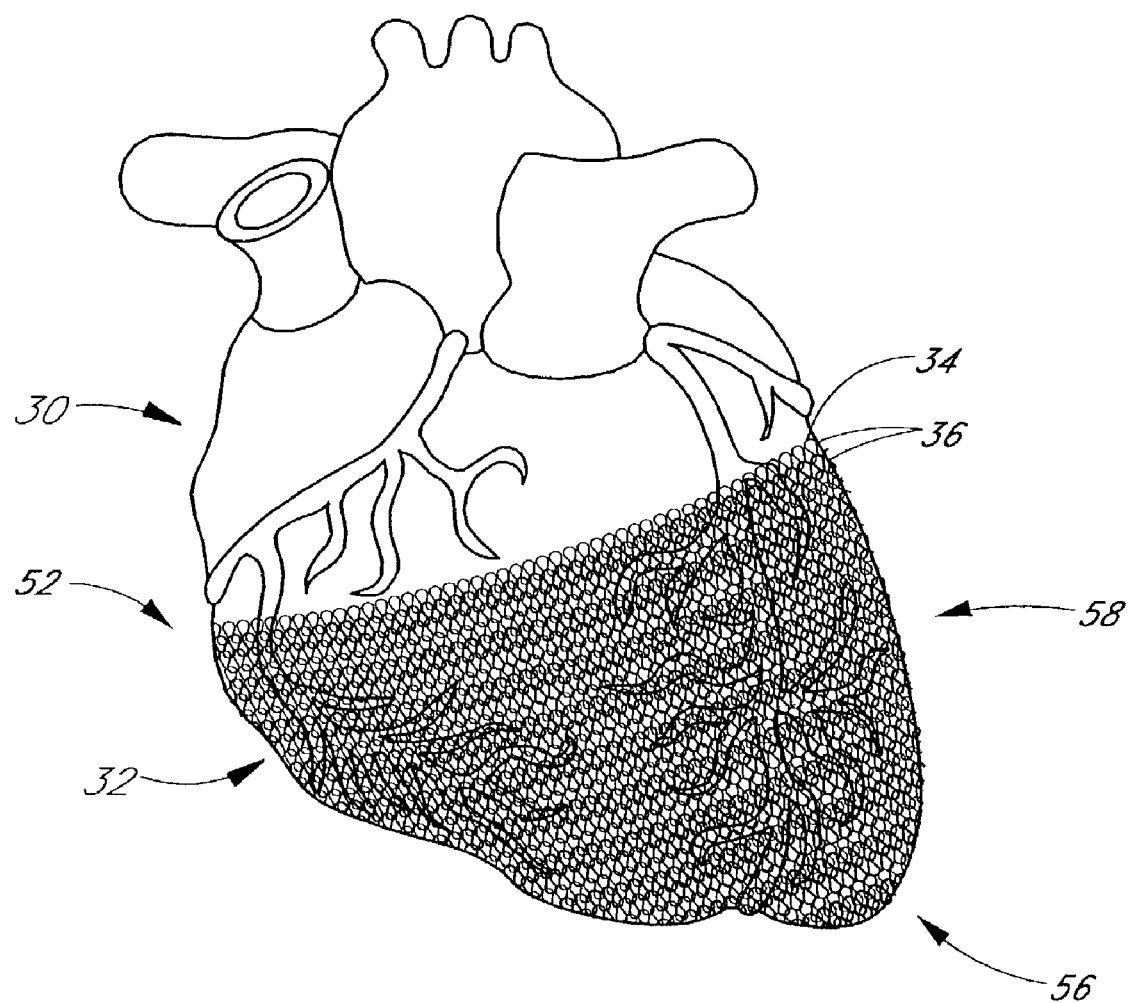
FIG. 1 is a schematic view of a heart with a cardiac harness placed thereon.

FIG. 1 illustrates a mammalian heart 30 having a cardiac wall stress reduction device in the form of a harness 32 applied to it. The cardiac harness 32 comprises a series of hinges or spring elements 34 that circumscribe the heart 30 and, collectively, apply a mild compressive force on the heart so as to alleviate wall stresses.

The term "cardiac harness" as used herein is a broad term that refers to a device fit onto a patient's heart to apply a compressive force on the heart during at least a portion of the cardiac cycle. Other devices that are intended to be fit onto a heart and are referred to in the art as "girdles," "socks," "jackets," or the like are included within the meaning of "cardiac harness."

Figure 2A:
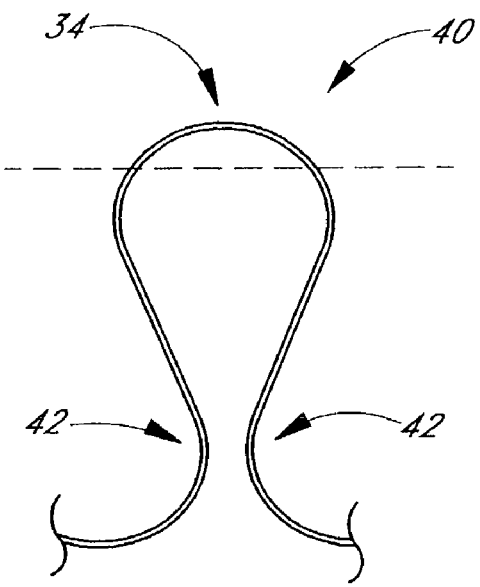
FIGS. 2A–2B illustrate a spring hinge in a relaxed position and under tension.
Figure 2B:
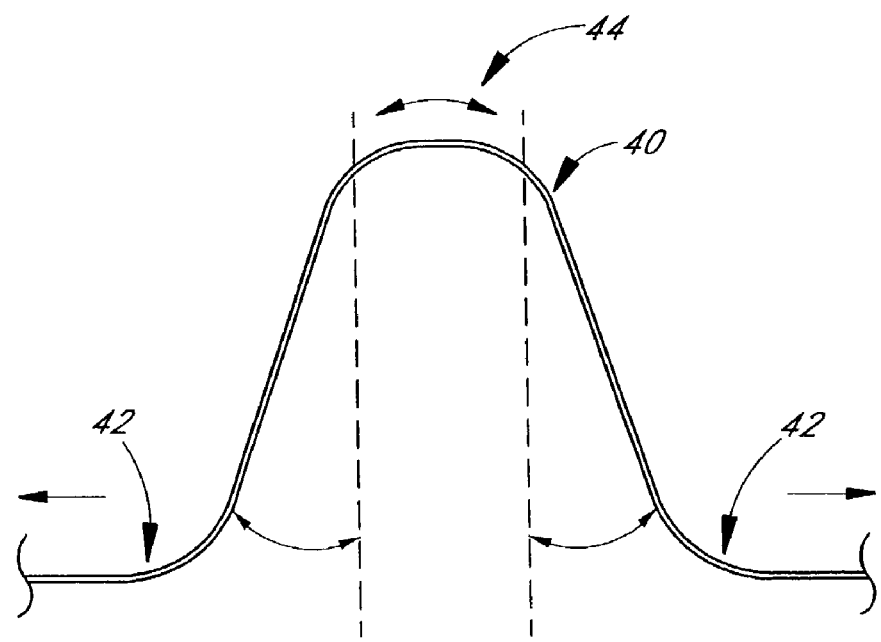

The cardiac harness 32 illustrated in FIG. 1 comprises at least one undulating strand 36 comprising a series of spring elements 34 referred to as hinges or spring hinges that are configured to deform as the heart 30 expands during filling. Each hinge 34 provides substantially unidirectional elasticity, in that it acts in one direction and does not provide much elasticity in the direction perpendicular to that direction. For example, FIG. 2A shows one embodiment of a hinge member 34 at rest. The hinge member 34 has a central portion 40 and a pair of arms 42. As the arms are pulled, as shown in FIG. 2B, a bending moment 44 is imposed on the central portion 40. The bending moment 44 urges the hinge member 34 back to its relaxed condition. Note that a typical strand comprises a series of such hinges, and that the hinges 34 are adapted to elastically expand and retract in the direction of the strand 36.

In the embodiment illustrated in FIG. 1, the strands 36 of spring elements 34 are constructed of extruded wire that is deformed to form the spring elements. Although FIG. 1 shows adjacent strands 36 interwoven one with another, it is to be understood that, in additional embodiments, adjacent strands 36 may not overlay or touch one another.

Figure 3:
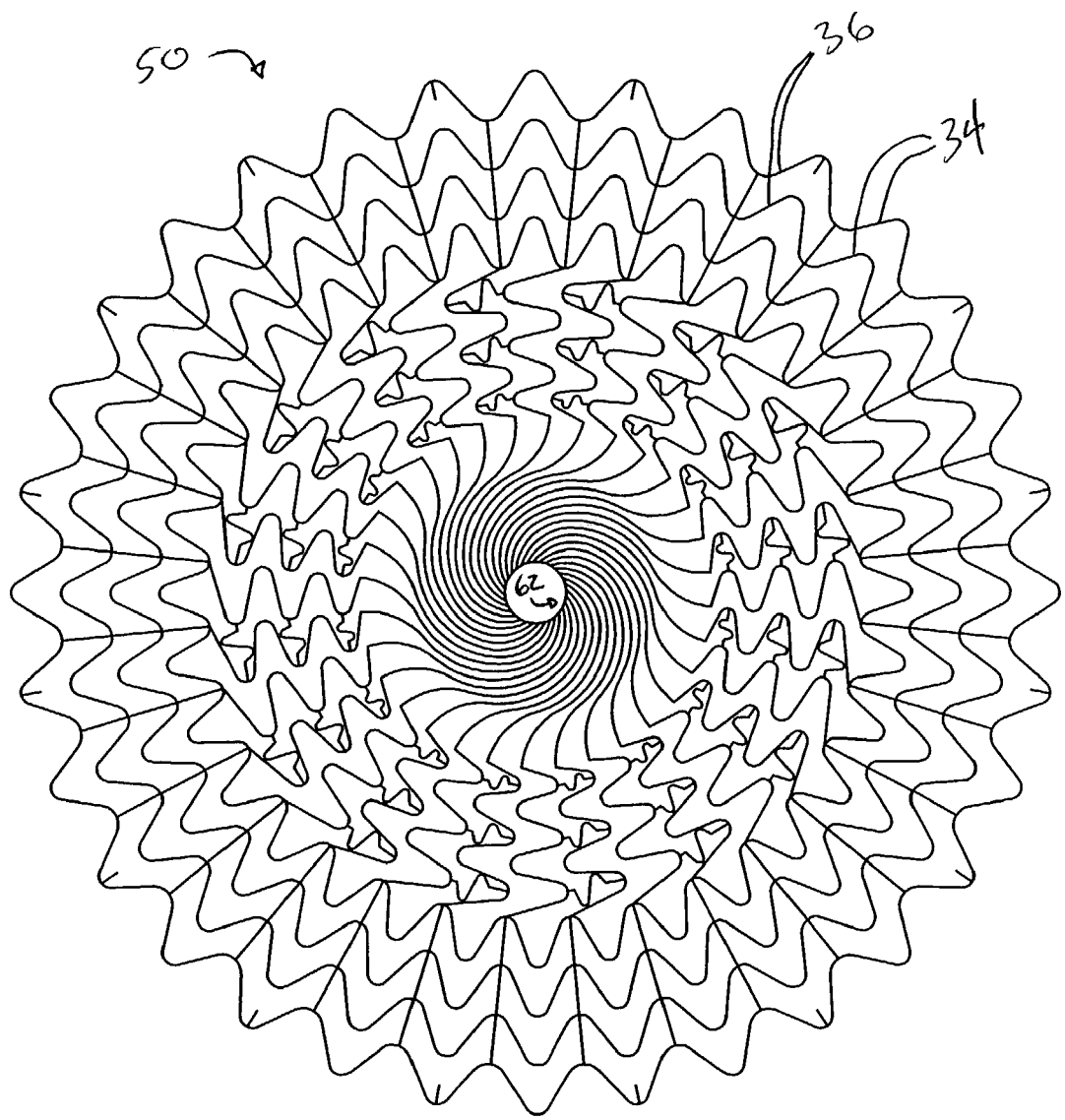
FIG. 3 shows an embodiment of a cardiac harness that has been cut out of a flat sheet of material.
Figure 4:
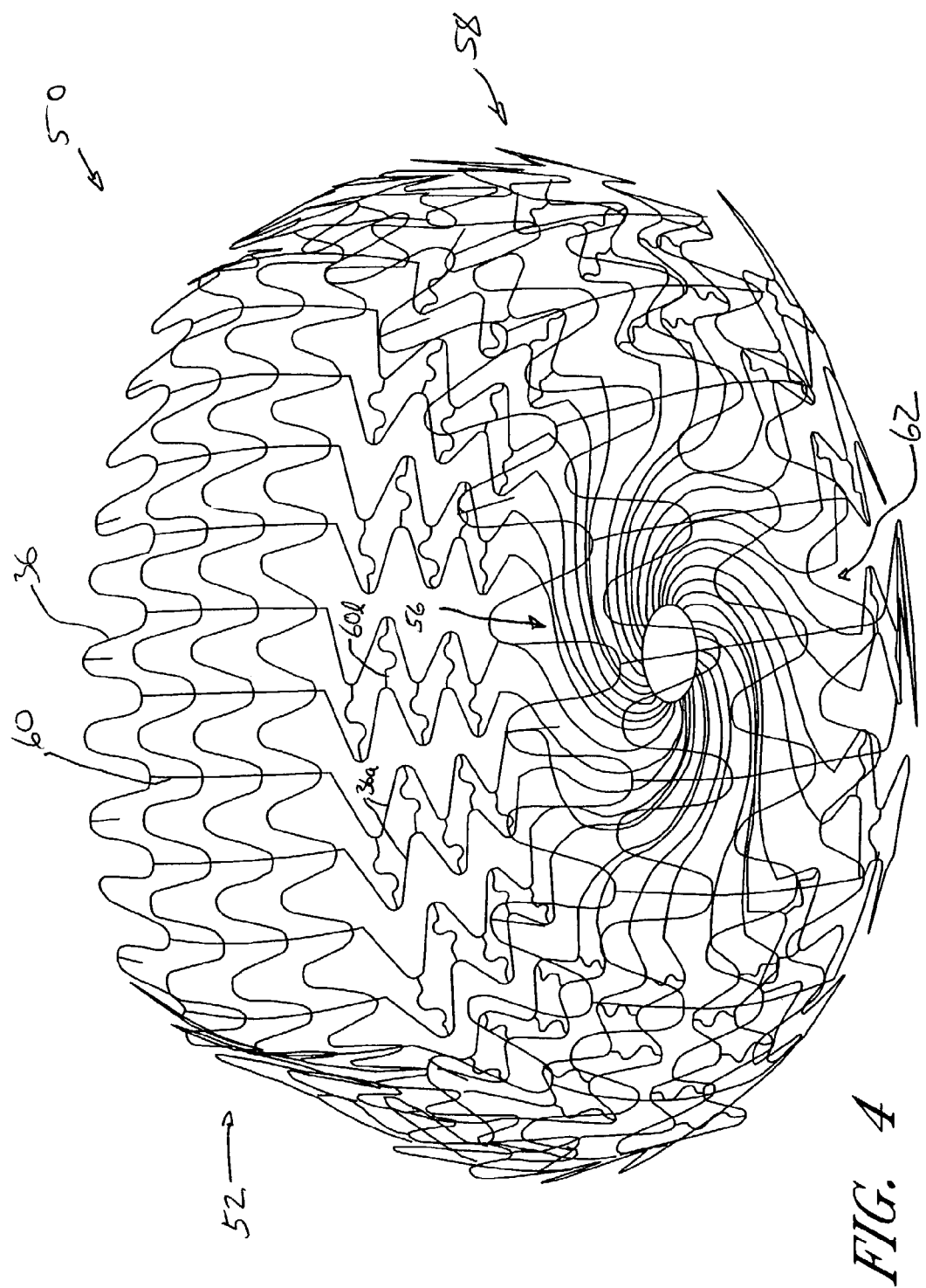
FIG. 4 shows the cardiac harness of FIG. 3 formed into a shape configured to fit about a heart.

FIGS. 3 and 4 illustrate another preferred embodiment of a cardiac harness 50, shown at two points during manufacture of such a harness. In the illustrated embodiment, the harness 50 is first formed from a relatively thin, flat sheet of material. Any method can be used to form the harness from the flat sheet. For example, in one embodiment, the harness is photochemically etched from the material; in another embodiment, the harness is laser-cut from the thin sheet of material. The embodiment shown in FIGS. 3 and 4 has been etched from a thin sheet of Nitinol, which is a superelastic material that also exhibits shape memory properties. The flat sheet of material is draped over a form, die or the like, and is formed to generally take on the shape of at least a portion of a heart.

With reference to FIGS. 1 and 4, the illustrated embodiments of the cardiac harnesses 32, 50 comprise a base portion 52, which is sized and configured to generally engage and fit onto a base region of a patient's heart; an apex portion 56, which is sized and shaped so as to generally engage and fit on an apex region of a patient's heart; and a medial portion 58 between the base and apex portions.

In the embodiment shown in FIGS. 3 and 4, the harness 50 comprises strands or rows 36 of undulating wire. As discussed above, the undulations comprise hinges/spring elements 34 which are elastically bendable in a desired direction. Some of the strands 36 are connected to each other by interconnecting elements 60. The interconnecting elements 60 help maintain the position of the strands 36 relative to one another. Preferably the interconnecting elements 60 allow some relative movement between adjacent strands 36.

As discussed above, the undulating spring elements 34 exert a force in resistance to expansion of the heart 30. Collectively, the force exerted by the spring elements tends toward compressing the heart, thus alleviating wall stresses in the heart as the heart expands. Accordingly, the harness helps to decrease the workload of the heart, enabling the heart to more effectively pump blood through the patient's body and enabling the heart an opportunity to heal itself. It should be understood that several arrangements and configurations of spring members can be used to create a mildly compressive force on the heart so as to reduce wall stresses. For example, spring members can be disposed over only a portion of the circumference of the heart or harness.

FIGS. 1–4 illustrate examples of cardiac wall tension reduction devices 30, 50. It is to be understood that several embodiments of tension reduction devices can have varying configurations, sizes, flexibilities, etc. As discussed in the above-referenced application, such wall tension reduction devices can be constructed from many suitable materials including various metals, fabrics, plastics and braided filaments. For example, a woven and/or knitted sock-like device can be used.

Experimental evidence indicates that application of a compressive or restrictive force can help a diseased heart resist enlargement. Such a compressive or restrictive force can be applied by any type or embodiment of a cardiac wall tension reduction device such as, for example, any cardiac harness 30, 50 embodiment disclosed above and/or in the above-referenced applications, a device similar to the Acorn CorCap™, or any type of cardiac sock or girdle.

When foreign objects or substances, such as a cardiac harness, are introduced onto or adjacent the heart, the body will tend to deposit tissue on or around the foreign object. For example, fibrin and collagen deposits will tend accumulate on and around the heart after a cardiac harness is placed thereon. This scar tissue tends to be tough, though flexible, and will additionally resist expansion of the patient's heart.

In one preferred embodiment, a cardiac wall tension reduction device is constructed of a bioabsorbable material. As such, the device will dissolve after a predetermined period of time. When in place, however, the device will relieve cardiac wall tension. Once the device is installed on the heart, the patient's body will respond by depositing scar tissue on the device and around the heart. Preferably, the tissue at least partially encapsulates the heart. After the device dissolves, the scar tissue remains. Thus, although the implanted device no longer restricts or resists further cardiac expansion, the scar tissue resists such expansion. As such, a long term treatment for resisting further cardiac expansion is established without requiring a permanent implant.

A bioabsorbable cardiac wall tension reduction device can be formed of any bioabsorbable material. It is to be understood that many types of materials can be used, including bioabsorbable materials typically used in sutures, stents and the like. For purposes of this disclosure, bioabsorbable materials include materials that degrade or dissolve over time when placed within a human body, and include biodegradable materials. In preferred embodiments, FDA-approved materials such as polylactic acid (PLA) and polyglycolic acid (PGA) can be used. Other materials, including both synthetic and naturally-derived polymers can suitably be employed.

A bioabsorbable cardiac harness can be formed in accordance with any acceptable method and fashion. For example, a sheet of PGA or PLA can be molded to a shape that fits about the heart. Similarly, a sheet can be formed having holes or gaps that lend themselves to increased flexibility. Further, a device can be molded or cut to have a series of undulating spring members, as in the embodiments discussed above. Still further, a lattice structure may be used to provide elasticity and facilitate and/or direct scar growth in a desired manner and direction. Still further, bioabsorbable material can be provided as extruded fibers or filaments that can be woven, braided, knit, or the like so as to fit about the heart and constrain expansion thereof.

As discussed in the above-referenced applications, when a force is applied to relieve cardiac wall stresses, the working load on the heart is reduced. Reducing the working load allows the heart to at least partially rest, and appears to provide an opportunity for the heart to at least partially heal itself. For example, it is anticipated that a remodeled diseased heart can reverse-remodel so as to become more healthy if cardiac wall stresses are reduced. The effect of reducing wall stress can indeed lead to valuable and beneficial healing consequences.

In another preferred embodiment, a cardiac wall tension reduction device can be at least partially made of a bioabsorbable material that is combined with medically-beneficial medicaments so that the beneficial medicaments are released as the bioabsorbable material dissolves. For example, bone marrow or stem cells can be provided so as to possibly stimulate myocardial regeneration. This type of treatment may help resolve an infarct, and promote healing of the heart. Of course, it is to be understood that any type of medicament anticipated to aid the heart can be combined with a bioabsorbable apparatus.

In another embodiment, a bioabsorbable cardiac harness can be combined with anti-fibrin drugs and/or other medications that resist the deposit or growth of body tissues around the installed harness. As such, the harness reduces heart wall stresses, giving the heart an opportunity to begin healing, but will not form extensive scar tissue. In this embodiment, the harness is adapted so that it will dissolve after a period of time sufficient to rest the heart so that it can continue its work without developing worsening symptoms of disease. Since little or no scar tissue is left behind after the harness dissolves, the rested heart will not be restricted by such tissue.

As discussed above, it is anticipated that the heart will reverse remodel when a harness reduces cardiac wall stress. As such, the heart may be smaller when a bioabsorbable harness dissolves than when the harness was installed. In accordance with one embodiment, a new, smaller harness is then be placed on the heart, thus prompting further reverse remodeling. This process can be repeated as often as desired, until the heart has reached a desired size and health level. When the desired size is achieved, further harnesses may not be needed because the heart is healthy enough to maintain its size. Alternatively, a permanent harness may be installed to maintain the heart at the desired size. In a further embodiment, another bioabsorbable harness is installed, but without anti-tissue-growth drugs. As such, the heart becomes at least partially encapsulated in body tissues that will resist enlargement of the heart from the desired size. This helps the heart maintain the desired healthy size.

In still another preferred embodiment, foreign bodies are introduced about the heart so as to stimulate tissue growth that will at least partially encapsulate the heart. These foreign bodies need not be in the form of a cardiac harness, and need not impart any compressive force on the heart. However, these foreign bodies will stimulate fibrin/collagen or other tissue growth about the heart so as to at least partially encapsulate the heart in the tissue. The tissue will act as a sock or jacket to resist further expansion of the heart.

It is to be understood that such foreign matter can be bioabsorbable, but is not necessarily so. For example, the foreign matter can comprise a liquid or powder irritant specially adapted to stimulate fibrin or collagen growth. Such irritants may include shredded or powderized polyester or other plastics.

In the embodiment shown in FIGS. 3 and 4, the harness 50 comprises strands 36 or strips of undulating wire. As discussed above, the undulations comprise hinges/spring elements 34 which are elastically bendable in a desired direction. The strands of spring elements are oriented in different directions and configured differently in the various portions of the harness. For example, as shown in FIGS. 3 and 4, in the base portion 52 of the harness, the strands are oriented so that the spring elements 34 will expand and contract in a direction generally transverse to a longitudinal axis of the heart. In the apex region 56, an "archimedes spiral" 62 configuration allows expansion and deformation in more than one direction, but is most compliant in a longitudinal direction. In the medial portion 58, strands 36a are oriented to expand and contract in a generally longitudinal direction. Additionally, some of the strands are connected to each other by interconnecting spring elements 601, which allow the adjacent strands to move relative to each other in a transverse direction. However, some of the strands 36a in the medial portion 58 are not connected to others of the strands and can move freely relative to one another in a transverse direction. Thus, in the medial portion, the strands are collectively expandable in directions between the longitudinal and transverse directions.

In a mammalian heart, the heart muscle cells in the base region tend to expand and contract in a generally transverse direction during pumping of the heart. In the apex region, the heart muscles tend to expand and contract in a longitudinal direction. Between the apex and base regions of the heart, the heart muscles generally expand and contract in directions between the longitudinal and transverse directions. In the embodiment illustrated in FIGS. 3 and 4, the spring elements are oriented generally in the directions of the cardiac muscle expansion so as to even better resist expansion and alleviate muscle stresses. As such, the arrangement of the base, medial and apex regions of the harness is specially adapted to accommodate the natural expansion and contraction of heart muscle tissue. In this manner, the harness generally mimics the directional contractions typical of heart muscle.

A harness having the above-described directional configuration helps to decrease the workload of the heart, enabling the heart to more effectively pump blood through the patient's body and enabling the heart an opportunity to heal itself. It should be understood, however, that other arrangements and configurations of spring members can be used to create a mildly compressive force on the heart so as to reduce wall stresses.

Figure 5:
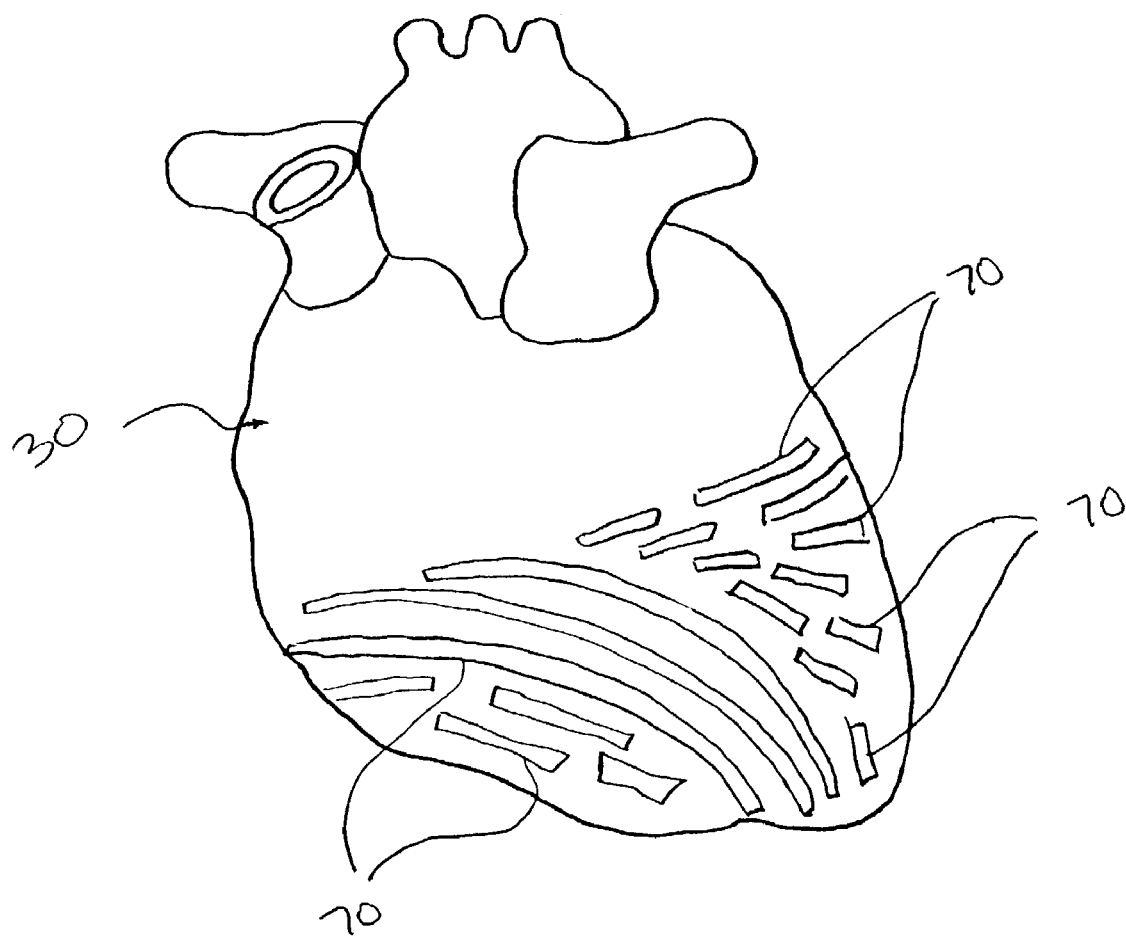
FIG. 5 illustrates a plurality of strips of foreign material arranged on a patient's heart.

In another embodiment, foreign matter or a cardiac harness can be arranged around the heart so as to stimulate tissue growth at specified locations and in desired directions. For example, matter can be placed so as to stimulate tissue growth in a configuration that generally follows the directional expansion and contraction of heart muscle. For example, in FIG. 5, foreign material is arranged on or around the heart 30 in a series of strips 70 which are arranged to generally correspond to the directional expansion and contraction of heart muscle. This prompts tissue growth in the area and directional configuration of the strips 70. As such, the tissue grows to generally correspond to the directional expansion and contraction of heart muscle. Such tissue will help reduce the muscle load as the heart expands during filling and contracts during pumping. Preferably, the foreign matter that stimulates the tissue growth comprises a bioabsorbable material. In another embodiment, the foreign matter is not bioabsorbable and is maintained permanently in the patient's body.

Introduction and placement of foreign material around the patient's heart can be performed via minimally-invasive methods. Minimally invasive methods can also be used to install a Nitinol, woven and/or bioabsorbable harness around the heart. Even less invasive methods can be used to place loose or detached foreign matter about the heart.

As a patient's heart enlarges during congestive heart failure, the annulus of certain valves, such as the mitral valve, tends to grow with the heart. Eventually, the valve annulus may increase in size to a point at which the leaflets are not large enough to completely close the valve. Another factor contributing to valve dysfunction is that as the heart enlarges, the geometry of the heart changes somewhat. Portions of the heart, such as the papillary muscles, are moved outwardly from the leaflets to which the papillary muscles are attached via the chordae tendinaea. These papillary muscles may be stretched so much that they prevent the valve leaflets from adequately approximating each other during valve closure. As such, the leaflets will not be able to fully close, and the valve will leak. Such valve leakage simply makes the patient's heart problems worse.

Figure 6:
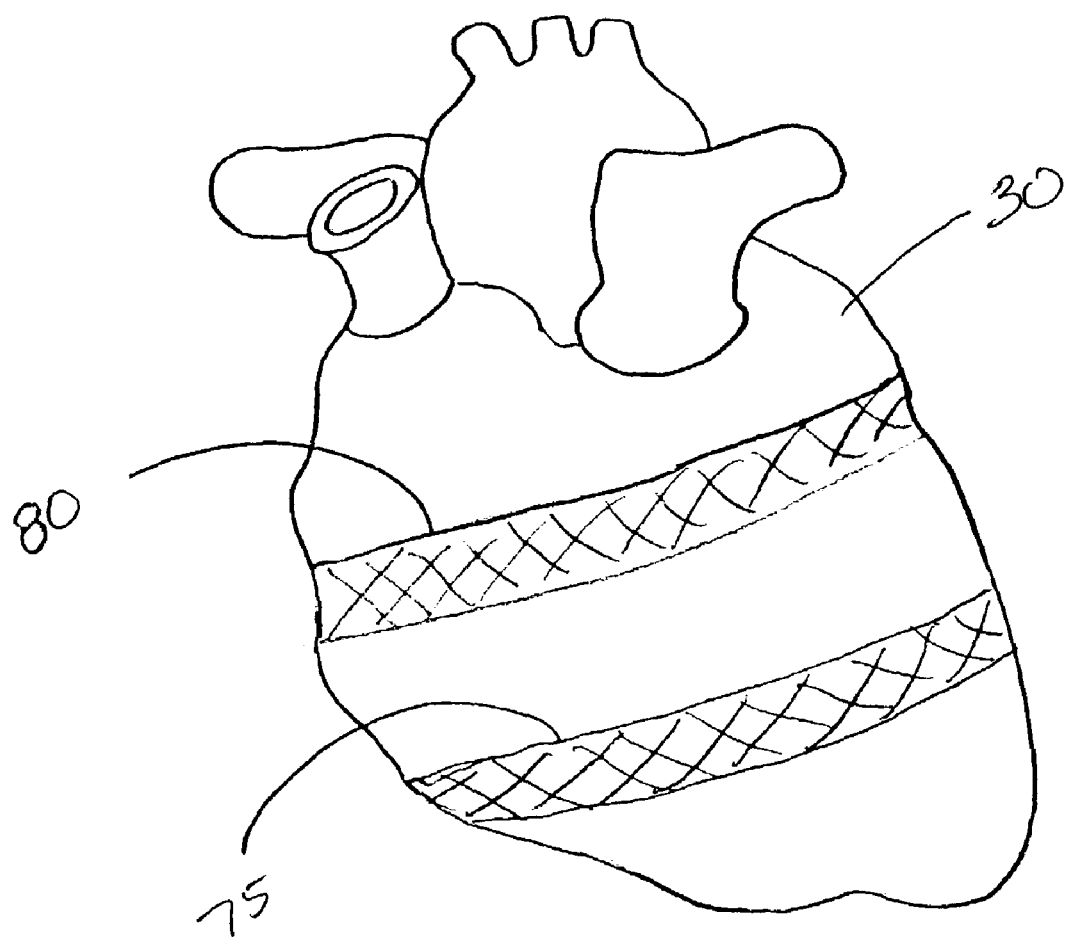
FIG. 6 illustrates an AV groove collar and papillary muscle band disposed on a patient's heart.

As discussed in the above referenced application entitled "Heart Failure Treatment Device and Method", a harness or collar can be configured to exert a compressive force on specific portions of a heart so as to help prevent or diminish valve dysfunction. For example, a collar-type device can be specially configured to fit around the AV groove region of the heart. FIG. 6 shows an AV groove collar arranged and configured to exert a compressive force that will tend to decrease the size of the valvular annuli and/or prevent enlargement of the valvular annuli beyond desired sizes.

With continued reference to FIG. 6, a papillary muscle band 75 can be configured to be placed around the heart 30 in the area of the papillary muscles. As known in the art, the papillary muscles are generally midway between the AV groove and the apex of the heart. Thus, a papillary muscle band 75 can exert a compressive force to reduce the diameter of the heart at the level of the papillary muscles. This will help the papillary muscles become less stretched so that they allow and facilitate closure of the valve leaflets. In the illustrated embodiment, the papillary band 75 is constructed of a woven or knitted fabric. It is to be understood that the papillary band can also have the undulating spring hinge construction of the embodiments discussed above.

As discussed above, a cardiac harness applies a mild compressive force on a patient's heart. It is anticipated that embodiments of an AV groove collar 80 and papillary muscle band 75 will exert a more aggressive compressive force than a typical cardiac harness. In another embodiment, a permanent cardiac harness implant is coated with an irritant in the portions configured to engage the AV groove and/or papillary muscle regions of the heart so as to produce a more dramatic stimulus for tissue growth in these portions. Thus, tissue growth in the AV groove and papillary muscle areas of the heart will be increased, providing further resistance to expansion in these areas.

In another embodiment, a bioabsorbable woven or knitted AV groove collar 80 stimulates tissue growth in and around the AV groove so as to provide similar benefits without a permanent implant. A bioabsorbable papillary muscle band 75 is similarly provided. The AV groove collar and papillary muscle band can be used independent of one another or in conjunction with one another and either independent of or in conjunction with a permanent or bioabsorbable cardiac harness. For example, a papillary muscle band can be placed on the heart before or after installation of a cardiac harness.

In still further embodiments, an AV groove collar and papillary band can be incorporated into a cardiac harness so as to apply specially-directed forces to the specific portions of the heart and to create specific regions of increased tissue growth.

In still another embodiment, an AV groove collar and/or papillary band is constructed of a bioabsorbable material and is configured to exert a force on a patient's heart within a first force range. A cardiac harness is provided and is configured to exert a force on the patient's heart within a second force range. The first range of force, which is to be exerted by the papillary band or AV groove collar, is greater than the second range. As such, when the combination is installed on the patient's heart, a greater force is exerted at the AV groove or papillary band region of the heart than elsewhere. As time passes and the collar or band is absorbed, the applied force on the heart becomes more equalized. This arrangement enables treatment of acute valvular dysfunction by applying a greater degree of force in one area of the heart than is needed for the rest of the heart. Over time, as the rest of the heart remodels, no extra force is needed to treat valvular dysfunction and, in this embodiment, is no longer exerted.

In a variation of the above embodiment, the AV groove collar and/or papillary muscle band is formed from a bioabsorbable material and is configured to have a maximum dimension beyond which the collar/band will not deform. As such, a selected portion of the heart can be constrained to a specific size while not so constraining the rest of the heart. This enables more passive treatment of the heart as a whole while addressing an acute issue. It is to be understood that, in other embodiments, a bioabsorbable member can temporarily apply a targeted, increased force in a desired portion of the patient's heart while an accompanying cardiac harness provides a more even, mild and permanent compressive force over a larger portion of the heart.

In the embodiments described above, the cardiac harness preferably applies a mild compressive force on the heart in order to achieve therapeutic benefits. An applied force or pressure within a therapeutic range is defined herein as a pressure of sufficient magnitude that, when applied to an organ such as the heart, results in a benefit to the organ. In one embodiment, the therapeutic range for a cardiac harness is between about 2–20 mmHg. More preferably, the therapeutic pressure is about 5–15 mmHg.

Figure 7:
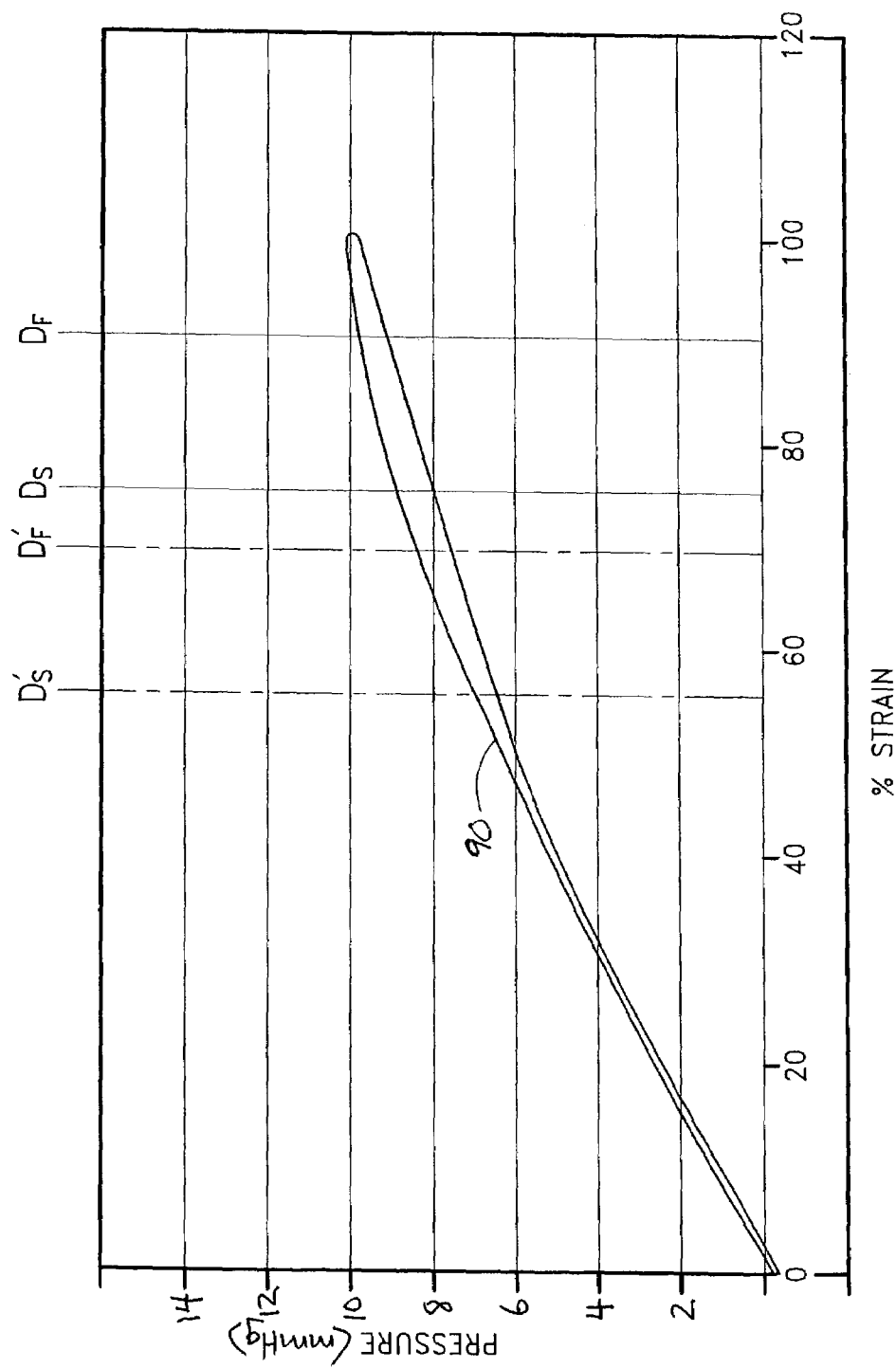
FIG. 7 shows a curve representing test data for one embodiment of a cardiac harness.

With next reference to FIG. 7, a pressure versus percentage strain curve 90 is presented reflecting actual test data for one embodiment of a cardiac harness constructed of drawn Nitinol wire formed into undulating spring hinges. As shown, this harness embodiment is capable of extensive deformation. In this embodiment, the harness is stretched from its original, at rest position in order to be fit over the patient's heart. When on the heart, it applies a mild, compressive force, which will tend to help the heart reverse-remodel. As the heart reverse-remodels and becomes smaller, the harness correspondingly becomes smaller. Of course, the size of the heart varies between the beginning of diastole and the end of diastole. In the illustrated embodiment, the labels $D_S$ and $D_F$ have been applied to the curve to identify the pressure applied by the harness at a particular level of strain $\epsilon$ corresponding to the beginning $D_S$ and end $D_F$ of diastole. In a similar manner the labels $D'_S$, and $D'_F$ illustrate the relative pressures applied by the harness at the beginning and end of diastole as the heart reverse remodels and becomes smaller. In the illustrated embodiment, the cardiac harness adjusts continuously with the heart as the heart changes in size, and also applies a therapeutic pressure to the heart even when the heart reverse remodels extensively.

In the illustrated embodiment, the cardiac harness exerts a pressure in response to strain of the harness. For example, if the harness is strained about 100%, it will exert about 10 mmHg on the heart. As the heart becomes smaller as a result of reverse remodeling, the percent strain of the harness will decrease, and the corresponding pressure exerted by the harness also will decrease. In the preferred embodiment, the harness is configured so that the applied pressure varies relatively little over a broad range of deformation. As such, the harness provides a therapeutic pressure even after the heart has reverse remodeled extensively.

For example, with continued reference to FIG. 7, a reduction in size corresponding to a 40% change in strain as the harness reduces from 100% to 60% strain is accompanied by a decrease in applied pressure of less than about 3 mmHg. A 40% change from 80% to 40% strain is accompanied by a decrease in applied pressure of less than about 4 mmHg. Still further, a 20% reduction in size can be accompanied by a decrease in applied pressure of less than about 3 mmHg or, depending on the degree of strain of the harness, less than about 2 mmHg. Additional changes in applied pressure corresponding to changes in the size/strain of the harness can be derived from the illustrated pressure/strain curve of FIG. 7.

In accordance with another embodiment, the harness represented by the test data of FIG. 7 is coated with a bioabsorbable coating including a medicament that inhibits growth of tissue in response to introduction of a foreign body. As such, scar tissue growth around the heart and harness will be minimized, and the harness can dramatically decrease in size as the heart reverse remodels without scar tissue preventing the harness from adjusting and changing shape with the patient's heart.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A method for treating heart failure of a patient, comprising:
   introducing a plurality of detached strips adjacent the heart each of said strips oriented generally corresponding to directional expansion and contraction of heart muscle to stimulate growth of scar tissue in a direction generally corresponding to directional expansion and contraction of heart muscle;
   the scar tissue at least partially ensapulating the heart and resisting expansion of the heart beyond a predetermined size.

2. The method of claim 1, wherein the plurality of detached strips comprise a bioabsorbable material.

3. The method of claim 1, wherein the plurality of detached strips are configured in the shape of a cardiac wall tension reduction device, which is configured to fit at least partially around the heart and to exert a generally inwardly directed force on the heart during at least a portion of the cardiac cycle.

4. The method of claim 1, additionally comprising placing the plurality of detached strips in a pattern to generally directionally mimic the directional expansion and contraction of heart muscle.

* * * * *